US009055763B2

(12) United States Patent
Leyer et al.

(10) Patent No.: US 9,055,763 B2
(45) Date of Patent: Jun. 16, 2015

(54) PROBIOTICS FOR USE IN RELIEVING SYMPTOMS ASSOCIATED WITH GASTRONITESTINAL DISORDERS

(75) Inventors: Gregory Leyer, Madison, WI (US); Arthur Ouwehand, Inga (FI)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 663 days.

(21) Appl. No.: 12/680,197

(22) PCT Filed: Oct. 8, 2008

(86) PCT No.: PCT/US2008/079177
§ 371 (c)(1),
(2), (4) Date: Oct. 7, 2010

(87) PCT Pub. No.: WO2009/048934
PCT Pub. Date: Apr. 16, 2009

(65) Prior Publication Data
US 2011/0033423 A1 Feb. 10, 2011

Related U.S. Application Data

(60) Provisional application No. 60/979,187, filed on Oct. 11, 2007.

(51) Int. Cl.
*A61K 49/00* (2006.01)
*A23L 1/30* (2006.01)

(52) U.S. Cl.
CPC .............. *A23L 1/3014* (2013.01); *A61K 35/745* (2013.01); *A61K 35/747* (2013.01)
USPC ........................................................ 424/9.1

(58) Field of Classification Search
CPC ..................................................... A23L 1/3014
USPC ........................................................ 424/9.1
See application file for complete search history.

(56) References Cited

U.S. PATENT DOCUMENTS

2004/0110270 A1   6/2004   Dennin et al.
2007/0148147 A1   6/2007   Dennin et al.

FOREIGN PATENT DOCUMENTS

| EP | 1010372 | 6/2000 |
|---|---|---|
| FR | 2848115 | 6/2004 |
| IT | WO2006/054135 | * 5/2006 |
| JP | 2000175615 | 6/2000 |
| WO | 2004009103 | 1/2004 |
| WO | 2004052462 | 6/2004 |
| WO | 2006032542 | 3/2006 |
| WO | 2006041930 | 4/2006 |
| WO | WO2006/097415 | 9/2006 |
| WO | WO2007/085970 | 8/2007 |

OTHER PUBLICATIONS

Sullivan et al. "*Lactobacillus acidophilus, Bifidobacterium lactis* and *Lactobacillus* F19 prevent antibiotic-associated ecological disturbances of *Bacterioides fragilis* in the intestine", J of Antimicrobial Chemotherapy, 2003, 52:308-311.*
Wildt et al. "Probiotic treatment of collagenous colitis: a randomized, double-blind, placebo-controlled trial with *Lactobacillus acidophilus* and *Bifidobacterium animalis* subsp. *Lactis*", Inflamm Bowel Dis., May 2006, 12(5):395-401.*
Longstreth G.F. et al., Functional bowel disorders, *Gastroenterology*, 2006, vol. 130, No. 5, p. 1480-1491.
O'Mahony L. et al., *Lactobacillus* and bifodiobacterium in irritable bowel syndrome: symptom responses and relationship to cytokine profiles, *Gastroenterology*, 2005, vol. 128, No. 3, p. 541-551.
Niedzielin K. et al., A controlled, double-blind, randomized study on the efficacy of *Lactobacillus plantarum* 299V in patients with irritable bowel syndrome, Eur. J. Gatroenterol. Hepatol., 2001, 13:1143-1147.
Wang, Weian et al., Probiotics and Irritable Bowel Syndrome, World China J Digest., Jan. 2004, vol. 12, No. 1 p. 172-176 (Abstract).
Sondergaard et al., "Effects of probiotic fermented milk on symptoms and intestinal flora in patients with irritable bowl syndrome: a randomized, placebo-controlled trial," *Sandinavian Journal of Gastroenterology*, 2011, vol. 46, pp. 663-672.
Simren et al., "Clinical trial: the effects of fermented milk containing three probiotic bacteria in patients with irritable bowel syndrome—a radomized, double-blind, controlled study," *Aliment Pharmacol. Ther.*, 2010, vol. 31, pp. 218-227.
Alm, Livia, et al. "Effect of a New Fermented Milk Product 'Cultura' on Constipation in Geriatric Patients", *The Lactic Acid Bacteria, Horizon Scientific Press, Ed: E.L. Foo et al.*, (1993), pp. 13-17.
Faber, Steven, et al. "The Use of Probiotics in the Treatment of Irritable Bowel Syndrome: Two Case Reports", *Alternative Therapies* (Jul/Aug. 2005) vol. 11, No. 4.

(Continued)

*Primary Examiner* — Bin Shen
(74) *Attorney, Agent, or Firm* — Steptoe & Johnson LLP

(57) ABSTRACT

The present invention provides probiotic compositions suitable for relieving symptoms associated with gastrointestinal disorders. In particular, the present invention provides compositions and methods to relieve symptoms associated with functional bowel disorders, irritable bowel syndrome, functional diarrhea, functional bloating, and other symptoms.

8 Claims, No Drawings

(56) References Cited

OTHER PUBLICATIONS

Fan, Yu-Jing, et al. "A probiotic treatment containing Lactobacillus, Bifidobacterium and Enterococcus improves IBS symptoms in an open label trial", *Zhejiang Univ Science B* (2006) vol. 7, No. 12, pp. 987-991.

Lukaczer, Dan "Case # 1051: A case Evaluating the Effect of Targeted Nutritional Support, including Lactobacillus acidophilus NCFM and Bifidobacterium lactis BI-07, in a Patient with Irritable Bowel Syndrome (IBS)", *Functional Medicine Research Center* (2004) https://nutri-dyn.com/images/LinkedCases/MET1051.pdf.

Sanders, M. E., et al. "Invited Review: The Scientific Basis of Lactobacillus acidophilus NCFM Functionality as a Probiotic", *J. Dairy Sci.* (2001) vol. 84, pp. 319-331.

Thompson, W.G., et al. "Functional bowel disorders and functional abdominal pain", *Gut* (1999) vol. 45 Suppl. II: 1143-1147.

Faber, "Irritable bowel syndrome and reinoculation with probiotics," *Amer. J. Gatroenterolo.*, (2002) vol. 97, S163.

Ringel et al., "Probiotic Bacteria Lactobacillus Acidophilus Ncfm and Bifidobacterium Lactic Bi097 Improve Syptons of Bloating in Pateints with Functional Bowel Disorders (FBD)," *Gastroenterol.*, Apr. 2008, vol. 134, A549.

American College of Gastroenterology, Functional Bowel Disorders, http://www.gastrori.com/ciocurnents/disease/functional.pdf downloaded Mar. 18, 2013.

Wikipedia Collagenous colitis, Mar. 6, 2013.

Majores M et al., "Mucosal atrophy in collagenous colitis: a case report", BMC Gastreoenterology, (2011) vol. 11, p. 114.

Poullis A P et al., "A new, highly sensitive assay for C-reactive protein can aid the differentiation of inflammatory bowel disorders from constipation- and diarrhea-predominant functional bowel disorders", European Journal of Gastroenterology & Hepatology, (Apr. 2002) vol. No. 4, p. 409-412.

"Evaluation of Nutritional Support with Lactobacillus acidophilus NCFM® and Bifidobacterium lactis BI-07 in Patients with Irritable Bowel Syndrome (IBS): Summary of Clinical Experience," Functional Medicine Research Center, (2004) MET 1080 Dec. 2004, and obtainable from the internet at: http://nutridyn.com/images/LinkedCases/MET1080.pdf.

Sindt RH, Danisco GRAS notification to US FDA, Sep. 2012.

Lukaczer D., "Case Study #1150: Evaluating the Effects of Specialized Nutritional Support, including Strain-Cartified Lactobacillus acidophilus NCFM® and Bifido bacterium lactis BI-07, in a Patient with Irritable Bowel Syndrome." Functional Medicine Research Center, (2005) 048IBS704, MET1150 Jun. 2005, and obtainable from the Internet at: http://nutri-dyn.com/images/LinkedCases/MET1150.PDF.

US Department of Agriculture, National Agriculture Library and National Academy of Sciences, Institute of Medicine, Food and Nutrition Board., Dietary Reference Intakes for Energy, Carbohydrate, fibre, Fat, Fatty Acids, Cholesterol, Protein, and Amino Acids (Macronutrients) (2005) chapter 7: Dietary, Functional and Total fibre, p. 339.

* cited by examiner

PROBIOTICS FOR USE IN RELIEVING SYMPTOMS ASSOCIATED WITH GASTRONITESTINAL DISORDERS

RELATED APPLICATIONS

The present application claims priority to U.S. Prov. Pat. Appln. Ser. No. 60/979,187, entitled "Probiotics for Use in Relieving Symptoms Associated with Gastrointestinal Disorders," filed Oct. 11, 2007.

FIELD OF THE INVENTION

The present invention provides probiotic compositions suitable for relieving symptoms associated with gastrointestinal disorders. In particular, the present invention provides compositions and methods to relieve symptoms associated with functional bowel disorders, irritable bowel syndrome, functional diarrhea, functional bloating, and other symptoms.

BACKGROUND OF THE INVENTION

Per the Rome Foundation (McLean, Va.), the Rome II diagnostic criteria for functional bowel disorders (FBD) refer to various symptoms localized to the mid or lower gastrointestinal (GI) tract. FBD include numerous clinical subgroups, such as irritable bowel syndrome (IBS), functional diarrhea, functional constipation, functional abdominal bloating, etc. These disorders are characterized by a variable combination of chronic or recurrent GI symptoms that are not due to structural or biochemical abnormalities in the affected patients. IBS is the most common functional GI disorder, affecting a large number of adults worldwide. As the pathophysiology of IBS and other FBDs is not well understood and currently available drug regimens are very limited, there remains a need for methods and compositions suitable for relieving the symptoms of these disorders.

SUMMARY OF THE INVENTION

The present invention provides probiotic compositions suitable for relieving symptoms associated with gastrointestinal disorders. In particular, the present invention provides compositions and methods to relieve symptoms associated with functional bowel disorders, irritable bowel syndrome, functional diarrhea, functional bloating, and other symptoms.

In some embodiments, the present invention provides a combination of *L. acidophilus* and *B. animalis* subsp. *lactis* Bi-07. In some preferred embodiments, the present invention provides a combination of *L. acidophilus* NCFM® (PTA-4797) and *B. animalis* subsp. *lactis* Bi-07 (PTA-4802). In some further particularly preferred embodiments, the present invention provides dietary supplements that contain *L. acidophilus* NCFM® and *Bifidobacterium lactis* Bi-07. In some further preferred embodiments, the dietary supplements containing *L. acidophilus* NCFM® and *Bifidobacterium lactis* Bi-07 are administered to subjects at a dosage in a range from about $1 \times 10^9$ CFU to about $2 \times 10^{11}$ CFU total probiotic bacteria/day. In some alternative embodiments the dosage is about $2 \times 10^{11}$ CFU total probiotic bacteria/day. However, it is not intended that the invention be limited to a specific dosage, as it is contemplated that different dosages will find use in different settings and/or with different patients.

The present invention also provides methods and compositions for use in improving the symptoms of bloating and distention in patients with FBD. In some preferred embodiments, the present invention provides compositions comprising *L. acidophilus* and *B. animalis* subsp. *lactis* and methods for their use in relieving the symptoms of FBD. In some particularly preferred embodiments, the present invention provides compositions comprising *L. acidophilus* NCFM® and *B. animalis* subsp. *lactis* Bi-07 and methods for their use in relieving the symptoms of FBD.

DESCRIPTION OF THE INVENTION

The present invention provides probiotic compositions suitable for relieving symptoms associated with gastrointestinal disorders. In particular, the present invention provides compositions and methods to relieve symptoms associated with functional bowel disorders, irritable bowel syndrome, functional diarrhea, functional bloating, and other symptoms.

In particular, the present invention provides probiotic cultures of *Lactobacillus* and *Bifidobacterium* suitable for use with human subjects. In some particularly preferred embodiments, *L. acidophilus* is provided in combination with *B. animalis*. In yet further embodiments, *B. animalis* subsp. *lactis* (also referred to as "*B. lactis*" herein) is provided in combination with *L. acidophilus* NCFM®. In still further particularly preferred embodiments, combinations of these organisms are provided. In yet additional embodiments, the *B. animalis* subsp. *lactis* (also referred to as "*B. lactis*" herein) is *B. animalis* subsp. *lactis* is the ATCC strain designated as PTA-4802, and the *L. acidophilus* NCFM® is the ATCC strain designated as PTA-4797.

During the development of the present invention, it was found that administration of these probiotics provided relief of GI symptoms. Thus, the present invention provides methods and compositions comprising a combination of these probiotic bacteria useful in relieving symptoms associated with FBD. In some particularly preferred embodiments, the compositions find use in relieving symptoms such as bloating and distension. However, it is not intended that the present invention be limited to these specific symptoms.

Definitions

Unless otherwise indicated, the practice of the present invention involves conventional techniques commonly used in food microbiology, nutritional supplements, gastrointestinal medicine, epidemiology, molecular biology, microbiology, protein purification, and industrial enzyme use and development, all of which are within the skill of the art. All patents, patent applications, articles and publications mentioned herein, both supra and infra, are hereby expressly incorporated herein by reference.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, definitions for a number of terms are provided below.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "food" refers to any nutritional item that provides nourishment to a plant and/or animal. It is not intended that the term be limited to any particular item, as it is used in reference to any substance taken into and assimilated by a plant or animal to keep it alive. It is also not intended that the term be limited to "solid" food, as liquid nourishment is encompassed by the definition. Indeed in some embodiments, liquid nourishment is preferred over solid food items. In some preferred embodiments, the term is specifically used in reference to food for human consumption.

As used herein, the term "feed" refers to any nutritional item that provides nourishment to non-human animals. It is not intended that the term be limited to any particular item, as it is used in reference to any substance taken into and assimilated by a plant or animal to keep it alive. It is also not intended that the term be limited to "solid" food, as liquid nourishment is encompassed by the definition. Indeed in some embodiments, liquid nourishment is preferred over solid food items.

As used herein, the terms "nutritional supplement" and "dietary supplement" refer to any product that is added to the diet. In some particularly preferred embodiments, nutritional supplements are taken by mouth and often contain one or more dietary ingredients, including but not limited to vitamins, minerals, herbs, amino acids, enzymes, and cultures of organisms. In some particularly preferred embodiments, the probiotics of the present invention are provided in the absence of additional bioactive compounds. As used here in "bioactive" refers to compositions/compounds that are active within the body. Bioactives include enzymes and other compositions that have various functions, including but not limited to increasing or decreasing absorption of nutritional substances, modifying the composition of and metabolic by-products from the intestinal microbiota, modifying the expression of the intestinal immune system, etc.

As used herein, the term "neutraceutical" refers to a food/dietary supplement that is believed and/or taken to provide health benefits.

As used herein, the term "probiotic" refers to a live microbial food ingredient that is beneficial to health.

As used herein, the term "prebiotic" refers to a non-digestible food ingredient that beneficially affects a human and/or other animal that ingests the prebiotic. In preferred embodiments, prebiotics selectively stimulate the growth and/or activity of a limited number of bacterial types in the intestinal tract, such that the health of the human and/or other animal is improved.

As used herein, the term "synbiotic" refers to a mixture of prebiotics and probiotics.

As used herein, the terms "illness" and "disease" refer to any deviation from or interruption of the normal structure and/or function of any body part, organ, or system that is manifested by a characteristic set of symptoms and signs. The term encompasses conditions with known or unknown etiology and/or pathology.

As used herein, the term "treating" refers to the providing of compositions that result in the improvement, amelioration, and/or remedying of a disease, disorder, or symptom of disease or condition.

As used herein, the terms "oral administration," and "per os" refer to the taking of food and/or supplements by mouth.

As used herein, the terms "prevention of illness" and "prevention of disease" refer to measures taken to avoid the incidence of illness/disease. In some embodiments, "prophylactic" measures are taken in order to avoid disease/illness.

As used herein, the term "symptom of disease" refers to any subjective of disease and/or a patient's condition. It is used in reference to any such evidence as perceived by the patient.

As used herein, the term "sign of disease" refers to an indication of the existence of disease/illness. It is used in reference to any objective evidence of disease that is perceptible to the examining physician and/or other healthcare provider.

As used herein, the terms "gastrointestinal" and "GI" refers to the stomach and intestines in the digestive tract of humans and other animals. However, as also used in context herein, the term "gastrointestinal tract" ("GI tract") refers to the entire alimentary canal, from the oral cavity to the rectum. The term encompasses the tube that extends from the mouth to the anus, in which the movement of muscles and release of hormones and enzymes digest food. The gastrointestinal tract starts with the mouth and proceeds to the esophagus, stomach, small intestine, large intestine, rectum and, finally, the anus.

As used herein, the term "digestive tract" refers to all of the organs and structures involved in the digestion of nutritional substances (e.g., food and drink), including the oral cavity, esophagus, stomach, small intestine, large intestine, and accessory organs (e.g., the liver, pancreas, etc.).

As used herein, the term "gastrointestinal flora" refers to the microorganisms that inhabit the gastrointestinal system of humans and other animals. In some particularly preferred embodiments, the term is used in reference to bacterial organisms, but it is not intended that the term be so limited.

As used herein, the term "bowel" refers to the intestines.

As used herein, the term "post-prandial" refers to the time after a meal. As used herein, the term "post-prandial symptoms" refers to symptoms that occur after a subject has ingested a meal.

As used herein, the term "functional bowel disorder(s)" ("FBD") refers to disorders comprising a variable combination of chronic or recurrent gastrointestinal symptoms that are not explained by structural or biochemical abnormalities present in the digestive tract of humans and/or other animals.

As used herein, the term "irritable bowel syndrome" ("IBS") encompasses the Rome II diagnostic criteria, as known in the art. In particular, the term is used in reference to at least 12 weeks (which need not be consecutive), in the preceding 12 months, of abdominal discomfort or pain that has at least two of the following three features: relief with defecation; and/or onset associated with a change in frequency of stool; and/or onset associated with a change in form (e.g., appearance) of stool. Symptoms that also support a diagnosis of IBS include: abnormal stool frequency (e.g., greater than 3 bowel movements per day and/or less than 3 bowel movements per week); abnormal stool form (e.g., lumpy/hard or loose/watery); abnormal stool passage (e.g., straining, urgency, and/or the feeling of incomplete evacuation); passage of mucus; and/or bloating and/or the feeling of abdominal distension.

As used herein, the term "functional abdominal bloating" encompasses the Rome II diagnostic criteria, as known in the art. In particular, the term is used in reference to at least 12 weeks (which need not be consecutive), in the preceding 12 months, of the feeling of abdominal fullness, bloating and/or visible distension; and insufficient criteria for a diagnosis of functional dyspepsia, irritable bowel syndrome, or another functional disorder.

As used herein, the term "functional constipation" encompasses the Rome II diagnostic criteria, as known in the art. In particular, the term is used in reference to at least 12 weeks (which need not be consecutive), in the preceding 12 months, with at least two of the following symptoms: straining during more than ¼ of defecations; lumpy or hard stools for more than ¼ of defecations; the sensation of incomplete evacuation for more than ¼ of defecations; the sensation of anorectal obstruction/blockage during more than ¼ of defecations; requiring manual maneuvers to facilitate more than ¼ of defecations (e.g., digital evacuation, support of the pelvic floor); and/or less than 3 defecations per week.

As used herein, the term "functional diarrhea" encompasses the Rome II diagnostic criteria, as known in the art. In particular, the term is used in reference to at least 12 weeks (which need not be consecutive), in the preceding 12 months, during which the subject experiences loose (e.g., mushy) or watery stools that are present more than ¾ of the time, but with no abdominal pain.

As used herein, the term "unspecified functional bowel disorder" encompasses the Rome II diagnostic criteria, as known in the art. In particular, it refers to bowel symptoms in the absence of organic disease that do not fit into the defined categories of functional bowel disorders.

As used herein, the term "relief from gastrointestinal symptoms" refers to reduced or termination of gastrointestinal symptoms, including but not limited to bloating, abdominal pain, diarrhea, etc.

As used herein, the term "morbidity" refers to illness/disease.

As used herein, the term "mortality" refers to death.

As used herein, the term "incidence" refers to the rate at which a certain event occurs, as in the number of new cases of a specific disease that occur during a certain period of time.

As used herein, the term "prevalence" refers to the total number of cases of a specific disease and/or condition in existence in a given population at a certain time.

As used herein, the term "sequelae" refers to illness/disease and symptoms/signs that occur as a consequence of a condition and/or disease event. In some embodiments, sequelae occur long after the initial disease/illness has resolved.

As used herein, the term "sub-clinical infection" refers to infection that does not result in the production/observation of signs or symptoms of disease. Often, the patient is infected with a disease-causing organism, but is unaware of the infection.

As used herein, the term "infection" refers to the invasion and multiplication of pathogenic microorganisms in the body.

As used herein, the term "culture" refers to any sample or item that contains one or more microorganisms. "Pure cultures" are cultures in which the organisms present are only of one strain of a particular genus and species. This is in contrast to "mixed cultures," which are cultures in which more than one genus and/or species of microorganism are present. In some embodiments of the present invention, pure cultures find use. For example, in some particularly preferred embodiments, pure cultures of *Lactobacillus* (e.g., *L. acidophilus*) find use. However, in alternative embodiments, mixed cultures find use. For example, in some particularly preferred embodiments, cultures comprised of *L. acidophilus* and *Bifidobacterium* find use.

As used herein, the term "*Lactobacillus*" refers to members of the genus *Lactobacillus*, in the family Lactobacillaceae. These bacteria are Gram-positive facultatively anaerobic bacteria that represent a major part of the bacterial group often referred to as "lactic acid bacteria." Various species of *Lactobacillus* have been identified, including but not limited to *L. acidophilus, L. bulgaricus, L. casei, L. delbrueckii, L. fermentum, L. plantarum, L. reuteri*, etc. While it is not intended that the present invention be limited to any particular species of *Lactobacillus*, in some particularly preferred embodiments, *L. acidophilus* NFCM finds use in the present invention. It is intended that the genus include species that have been reclassified (e.g., due to changes in the speciation of organisms as the result of genetic and other investigations) or renamed for marketing and/or other purposes.

As used herein, the term "*Bifidobacterium*" refers to members of the genus *Bifidobacterium*. These bacteria are Gram-positive anaerobic bacteria that are one of the major strains of bacteria present in the gastrointestinal flora. While it is not intended that the present invention be limited to any particular species of *Bifidobacterium*, in some particularly preferred embodiments, *B. lactis* Bi-07 finds use in the present invention. It is intended that the genus include species that have been reclassified (e.g., due to changes in the speciation of organisms as the result of genetic and other investigations) or renamed for marketing and/or other purposes.

As used herein, the term "antimicrobial" refers to any compound which inhibits the growth or kills microorganisms. It is intended that the term be used in its broadest sense and includes, but is not limited to compounds such as antibiotics produced naturally or synthetically. It is also intended that the term encompass compounds and elements that are useful for inhibiting the growth of or killing microorganisms.

As used herein, the terms "microbiological media," "culture media," and "media" refer to any suitable substrate for the growth and reproduction of microorganisms. The term encompasses solid plated media, as well as semi-solid and liquid microbial growth systems.

EXPERIMENTAL

The following example is provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); $H_2O$ (water); gm (grams); µg and ug (micrograms); mg (milligrams); ng (nanograms); µl and ul (microliters); ml (milliliters); mm (millimeters); nm (nanometers); µm and um (micrometer); M (molar); mM (millimolar); µM and uM (micromolar); U (units); sec (seconds); min(s) (minute/minutes); hr(s) (hour/hours); sd and SD (standard deviation); PBS (phosphate buffered saline [150 mM NaCl, 10 mM sodium phosphate buffer, pH 7.2]); w/v (weight to volume); v/v (volume to volume); CFU (colony forming units); y/o (years old; years of age); Becton Dickinson (Becton Dickinson Diagnostic Systems, Sparks, Md.); (Difco Laboratories, Detroit, Mich.); GIBCO BRL or Gibco BRL (Life Technologies, Inc., Gaithersburg, Md.); UNC (University of North Carolina); and ATCC (American Type Culture Collection, Manassas, Va.).

The organisms used in the development of the present invention were *L. acidophilus* NCFM® (PTA-4797) and *B. animalis* subsp. *lactis* Bi-07 (PTA-4802). These strains were grown at 37° C., in MRS medium (e.g., Difco, Becton Dickinson) containing 0.05% cysteine. Cultures were incubated for 48-72 hours in BBL GASPAK™ anaerobic jars containing $H_2/CO_2$ atmosphere (Becton-Dickinson). For large-scale production, the strains were grown in fermentation media, harvested by centrifugation and cryostabilized using methods known in the art. The cryostabilized solution was lyophilized.

The present invention was assessed using a prospective, randomized, double-blind, placebo controlled study to evaluate the efficacy of probiotic (Lactobacillus and *Bifidobacterium*) bacteria in patients with FBD. The total study duration was 14 weeks. There was a 2 week screening period to determine eligibility, predominant symptoms, and severity at baseline. This was followed by an 8-week treatment phase, in which patients were randomized into 2 treatment arms (i.e., active treatment with the probiotic supplement or placebo). The randomization was kept blinded to the patient and the investigators. There was also a 4-week follow-up phase after discontinuation of the treatment phase.

Subjects were recruited from the outpatient GI clinic at the University of North Carolina Hospitals, from local clinic facilities, and by advertisement. Power calculations for this study were based on reported effects of probiotics on abdominal pain (See e.g., Niedzielin et al., Eur. J. Gatroenterol. Hepatol., 13:1143-1147 [2001]) since it is a fundamental symptom of IBS. Power calculations indicated that the study was adequately powered.

Subjects meeting all of the following inclusion criteria were determined to be eligible for this study: signed informed consent was received; 18-65 years of age; ambulatory outpatient; presence of IBS, or functional diarrhea, or functional bloating according to the Rome II criteria for functional GI disorders and the subject has had the above symptoms for at least two weeks, despite current therapy (for patients with diarrhea, the definition of a mean of ≥2 bowel movements per day, or a mean score of ≥4 on the Bristol Stool Form Scale per week was used); the subject's symptoms were mild to moderate symptoms in severity (symptoms severity was assessed at baseline and at the end of the 2-weeks screening period to determine eligibility prior randomization); the subject has had a normal flexible sigmoidoscopy or colonoscopy within the last 5 years (subjects must have had a colonoscopy if age >50 y/o).

Potential subjects were excluded if any of the following criteria applied: the subject had inflammation or structural abnormality of the digestive tract (e.g., inflammatory bowel disease (IBD), duodenal ulcer (DU) or gastric ulcer (GU), obstruction, or symptomatic cholelithiasis); the subject had severe FBD related symptoms at baseline; the subject has a serious, unstable medical condition; the subject has insulin-dependent diabetes mellitus; the subject had a major psychiatric diagnosis or a suicide attempt within the last two years; the subject had a history of alcohol or substance abuse within two years; the subject has abnormal laboratory results (including ALT or AST >than 2.5 times normal, serum creatinine >2.0 mg/dl, untreated abnormal TSH value); the subject had been treated for a malignancy within the last 5 years (except BCC or SCC skin cancer); the subject had been diagnosed with lactase deficiency and this could have explained their symptoms (i.e., symptoms resolved or reduced significantly with lactose-free diet); the subject participated in a drug study within the last 21 days; the subject received antibiotic treatment during the last 8 weeks (for subjects on antibiotic treatment, a washout period of 8 weeks was required); the subject had previous significant gastric or intestinal surgery; or the subject was pregnant or lactating, or unwilling to maintain effective contraception during course of the study.

Fifty-seven (57) randomized subjects (females and males) who fulfilled the Rome II criteria for functional bowel disorders (FBD), IBS, or functional diarrhea, and who had at least 6 months of recurrent symptoms were included in this study. Of these, 30 were randomized to the active treatment group and 27 were assigned to the placebo group. Of these individuals, 33 were IBS patients (17 in the active group and 16 in the placebo group); 21 were FBD patients (non-IBS FBD) (12 in the active group and 9 in the placebo group); 3 were functional diarrhea patients (1 in the active group and 2 in the placebo group). The following table provides demographic information for each of the individuals in the active and placebo groups.

TABLE 1

Demographics of Active and Placebo Groups

| | Active Group (n = 30) | Placebo Group (n = 27) |
|---|---|---|
| Age (mean; S.D.) | 36.0; 10.9 | 37.0; 14.7 |
| Sex (% female) | 72.4 | 71.4 |
| Education Level (% in each category): | | |
| Some High School | 3.3 | 0.0 |
| High School Graduate | 30.0 | 7.4 |
| Some College or Technical School | 23.3 | 40.7 |
| Completed 4 Years of College | 20.0 | 25.9 |
| Some Graduate School | 23.3 | 11.1 |
| Completed Graduate Degree | 3.3 | 14.8 |
| Race/Ethnicity: | | |
| Asian | 0.0 | 7.4 |
| African-American | 16.7 | 3.7 |
| White | 83.3 | 85.2 |
| Other | 0.0 | 3.7 |
| Relationship Status: | | |
| Single/Never Married | 46.7 | 53.6 |
| Married/Cohabiting | 46.7 | 39.3 |
| Separated/Divorced | 6.7 | 7.1 |

Subjects were seen in the clinic 4 times during this study: (1) at the beginning of the screening period (week −2); (2) at the beginning of the treatment phase (week 0); (3) midway through the treatment phase (week 4); and (4) at the end of the treatment phase (week 8). Subjects were contacted by phone two weeks (week 10) and four weeks (week 12) after completion of the treatment phase. In each of the study visits, subjects were evaluated for the primary and secondary outcome measures using the following tools: GSA ("gastrointestinal symptom-specific anxiety") Dem Med ("major medical descriptors") (visit 1 only); onset of symptoms questionnaire (visit 1 only); antibiotic/probiotic treatment questionnaire (visit 1 only); satisfaction scale; BDI-II ("Beck Depression Inventory-II); Quality Of Life (IBS-QOL); eating associated symptoms questionnaire; IBS severity index; concomitant medications; and review of adverse events.

During (week 12) and at the end (i.e., week 14) of the follow-up phase subjects were contacted by phone and asked to mail back their daily diary cards. Subjects were asked to record their symptoms on diary cards starting at the beginning of the screening period and ending 4 weeks after treatment was discontinued. Subjects recorded the number of bowel movements, stool consistency for each bowel movement, abdominal pain, bloating, and post-prandial symptoms. In addition, subjects recorded the number of pills taken each day. During the phone calls, subjects were asked about the global relief of their functional GI symptoms, overall well being, concomitant medications, and about the status of any adverse events from the study (if there were any). The subjects' symptoms were then rated on a daily basis.

All of the subjects underwent various laboratory tests, including a breath test to assess for bacterial overgrowth and lactose intolerance during the screening period (week −2 to 0). Those with negative results obtained during the last 24 months were acceptable; those patients who were found positive were excluded. Blood tests were conducted to evaluate for treatment safety, at the end of screening and prior to starting treatment (week 0) (baseline), midway through treatment (week 4) and at the end of treatment (8 weeks). This included ESR (erythrocyte sedimentation rate) as a marker of inflammation, complete blood count with platelets and differential (hematocrit, hemoglobin, red blood cell count, white blood cell count, and differential to include: neutrophils, lymphocytes, monocytes, eosinophils, basophils, bands), sodium, chloride, potassium, calcium, phosphorus, creatinine, BUN, total protein, LFTs, albumin, and blood pregnancy test. Laboratory results obtained within six months of the screening visit were be allowed to be used as baseline values. The laboratory results were recorded for each patient. Although investigation of fecal microflora was an option, the decision was made not to conduct this aspect of investigation, although it is an aspect that could be included in subsequent investigations.

As indicated above, subjects were enrolled into one of two treatment arms, namely active treatment vs. placebo. The active treatment group received supplements containing *L. acidophilus* NCFM® and *Bifidobacterium lactis* Bi-07. Patients in the active treatment group received oral doses of equivalent amounts each organism at $1 \times 10^{11}$ total CFU ($5 \times 10^{10}$ CFU per strain). The placebo and probiotic products were administered in twice per day in capsule form, for a total daily dose of $2 \times 10^{11}$ CFU.

Throughout the study, the subjects were allowed to maintain their current, stable (≥1 month) medications (these included antispasmodics, fiber supplements, antidiarrheal and/or laxative medications, and antidepressants). However, those patients currently on "anti-gas" medications for their bowel symptoms, were asked to discontinue these medications at least 7 days prior to screening visit (i.e., subjects were not allowed to take these medications within the last week prior entering the screening phase of the study). For those taking antibiotics for any reason, a washout period of at least 8 weeks was required prior to enrolment in the study. Subjects were also required to remain off these medications during the remainder of the study. Participants were asked to keep the same medications to avoid any change in their stable medications and to avoid taking any medication on an as-needed (i.e., PRN) basis during study participation. Change in medications during the study period was reviewed in each study visit and recorded. In addition, subjects were allowed to consume unintentional probiotics (i.e., yoghurts). However, they were asked to avoid bacteria-enriched yoghurts and fermented milks during the study. In addition, probiotic supplements were not allowed during the study and subjects were asked to discontinue these supplements at least 8 weeks prior to enrollment in the study.

Data analysis was performed to evaluate significant change in all outcome measures scores and laboratory tests between pretreatment (i.e., the end of the screening phase [week 0]), completion of the treatment phase (week 8), and completion of follow-up period (week 12). Assessments were made for the responsiveness of each of the specific endpoint measures in order to determine the overall responsiveness and the most specific/positive symptom response. Measure of responsiveness included global relief of functional GI symptoms, all specific functional GI related symptoms, IBS severity index, and health related quality of life. Analysis was conducted for the whole FBD group and, in an exploratory manner, separately for each subgroup (i.e., IBS, functional diarrhea, and non-IBS functional bowel disorder). The tolerability and safety of the treatment was analyzed with respect to the incidence of adverse events and changes in laboratory tests. An updated log of reported adverse events and laboratory abnormalities for each patient and for the whole study population was kept.

The results indicated that bloating and distention improved significantly in the probiotics treatment group, as compared to the placebo group at 4 weeks ($4.10 \pm 3$ vs. $17 \pm 3$, p=0.009, respectively), and showed a strong trend of improvement at 8 weeks ($4.26 \pm 3$ vs. $5.84 \pm 3$, p=0.06, respectively). Secondary analyses using only the IBS subgroup (n=33) showed similar results with significant improvement in bloating and distention in the probiotics group (n=17), as compared to the placebo (n=15) group ($4.24 \pm 3$ vs. $6.73 \pm 3$, p=0.03, respectively). These results indicated that dietary supplements containing *L. acidophilus* NCFM® and *Bifidobacterium lactis* Bi-07 ($2 \times 10^{11}$ CFU total probiotic bacteria/day) significantly improved symptoms of bloating and distention in patients with FBD. Thus, it is contemplated that these probiotics will find use in the management of patients with these disorders. Importantly, it is noted that these probiotics were provided to the subjects without the addition of other bioactives.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method for improving the symptoms of functional bowel disorder, comprising: i) providing an individual having functional bowel disorder; ii) providing a composition comprising a probiotic, wherein said probiotic consists of *L. acidophilus* and *Bifidobacterium lactis*; and iii) administering only said composition to said individual under conditions such that said symptoms of functional bowel disorder are improved, wherein said symptoms of functional bowel disorder comprise bloating and distention.

2. The method of claim 1, wherein said composition is a dietary supplement.

3. The method of claim 1, wherein said *L. acidophilus* and *Bifidobacterium lactis* are administered to said individual at a dosage of from about $1\times10^9$ to about $2\times10^{11}$ CFU total probiotic bacteria/day.

4. The method of claim 1, wherein said *L. acidophilus* and *Bifidobacterium lactis* are administered to said individual at a dosage of about $2\times10^{11}$ CFU total probiotic bacteria/day.

5. The method according to claim 1, wherein the *Lactobacillus acidophilus* is *L. acidophilus* NCFM (PTA-4797).

6. The method according to claim 1, wherein the *Bifidobacterium lactis* is *B. animalis* subsp. *Lactis* Bi-07 (PTA-4802).

7. A method for improving the symptoms of functional bowel disorder, comprising: i) providing an individual having functional bowel disorder; ii) providing a composition comprising a probiotic, wherein said probiotic comprises *L. acidophilus* NCFM (PTA-4797) and *B. animalis* subsp. *lactis* Bi-07 (PTA-4802); and iii) administering said composition to said individual under conditions such that said symptoms of functional bowel disorder are improved, wherein said symptoms of functional bowel disorder comprise bloating and distention.

8. A method for improving the symptoms of functional bowel disorder, comprising: i) providing an individual having functional bowel disorder; ii) providing a composition comprising *L. acidophilus* and *Bifidobacterium lactis* in the absence of additional bioactive compounds; and iii) administering said composition to said individual under conditions such that said symptoms of functional bowel disorder are improved, wherein said symptoms of functional bowel disorder comprise bloating and distention.

* * * * *